(12) United States Patent
Angres

(10) Patent No.: US 10,094,813 B2
(45) Date of Patent: Oct. 9, 2018

(54) METHOD FOR INVESTIGATING THE SHELF LIFE OF FOOD IN PACKAGING

(71) Applicant: Steinfurth Mess-Systeme GmbH, Essen (DE)

(72) Inventor: Johann Angres, Bochum (DE)

(73) Assignee: Steinfurth Mess-Systeme GmbH, Essen (DE)

( * ) Notice: Subject to any disclaimer, the term of this patent is extended or adjusted under 35 U.S.C. 154(b) by 163 days.

(21) Appl. No.: 14/917,951

(22) PCT Filed: Sep. 9, 2014

(86) PCT No.: PCT/EP2014/069188
§ 371 (c)(1),
(2) Date: Mar. 10, 2016

(87) PCT Pub. No.: WO2015/036399
PCT Pub. Date: Mar. 19, 2015

(65) Prior Publication Data
US 2016/0223508 A1    Aug. 4, 2016

(30) Foreign Application Priority Data

Sep. 10, 2013    (DE) .......................... 10 2013 109 945

(51) Int. Cl.
*G01N 33/14*    (2006.01)
(52) U.S. Cl.
CPC ........... *G01N 33/14* (2013.01); *G01N 33/143* (2013.01); *G01N 33/146* (2013.01)
(58) Field of Classification Search
CPC ...... G01N 1/2226; G01N 33/02; G01N 33/14; G01N 33/143; G01N 33/146
(Continued)

(56) References Cited

U.S. PATENT DOCUMENTS 5,426,593 A * 6/1995 Seiden .................. G01N 27/49
                                                      702/24
5,473,161 A  12/1995 Nix et al.
(Continued)

FOREIGN PATENT DOCUMENTS

EP         1626275        9/2007
WO    WO 2015/036399     3/2015

OTHER PUBLICATIONS

International Search Report and the Written Opinion dated Oct. 27, 2014 From the International Searching Authority Re. Application No. PCT/EP2014/069188.
(Continued)

*Primary Examiner* — Benjamin Schmitt

(57) ABSTRACT

A method for investigating the shelf life of food in packaging. The method includes the following to be carried out: a) creating at least one reference measurement with: a direct and indirect sample measurement at the time, repetition of the direct and indirect sample measurement at predefined intervals of time, storage of the reference measurement results of the sample measurements; creating a comparison measurement with: at least one indirect sample measurement at the time, comparison of the indirect measurement result with the corresponding reference measurement result from the comparison time, performance of at least one direct sample measurement at the time if a deviation of the comparison result from step is exceeded, repetition of the indirect sample measurement at predefined intervals of time, storage of the measurement results of the sample measurements.

13 Claims, 2 Drawing Sheets

(58) Field of Classification Search
USPC ................ 73/19.06, 40, 45.4, 49.2, 49.3, 52
See application file for complete search history.

(56) References Cited

U.S. PATENT DOCUMENTS 6,964,191 B1    11/2005  Tata
2006/0032293 A1*  2/2006  Wild ...................... G01N 33/14
                                                                                           73/38

OTHER PUBLICATIONS

Ivorra et al. "Detection of Expired Vacuum-Packed Smoked Salmon Based on PLS-DA Method Using Hyperspectral Images", XP055132038, Journal of Food Engineering, 117(3): 342-349, Aug. 1, 2013. Para [02.1]-[02.2].

* cited by examiner

METHOD FOR INVESTIGATING THE SHELF LIFE OF FOOD IN PACKAGING

RELATED APPLICATIONS

This application is a National Phase of PCT Patent Application No. PCT/EP2014/069188 having International filing date of Sep. 9, 2014, which claims the benefit of priority of German Patent Application No. 2013 109 945.9 filed on Sep. 10, 2013. The contents of the above applications are all incorporated by reference as if fully set forth herein in their entirety.

SUMMARY OF THE INVENTION

The present invention is directed at a method for investigating the shelf life of food stuffs in packagings according to the preamble of claim 1. Furthermore the present invention relates to a device for investigating the shelf life of food stuffs in packagings according to the preamble of claim 15. A device of this kind may comprise a mechanical mounting for the packaging and a measuring head as well as an evaluation unit.

Various methods for investigating the shelf life of food stuffs in packagings are known from the art. Such methods relate for example to any type of drink and milk products in the form of cheese, yogurt and meat products, sweets, spices and similar. The best-before-date (called BBD for short) of food producers for their foods indicates the date, by which the food, if correctly stored (in particular if the storage temperature specified in conjunction with the best-before date is adhered to) has definitely to be consumed without significant losses in taste and quality and without health risk. The best-before date is not an expiry date since, as a rule, the foods are still edible after the specified best-before date.

Food producers take samples from each food series produced, by means of which they can prove the quality of a series of the food products, in order to be able to furnish evidence to the contrary, when countering possible compensation claims by consumers, in a legally safe manner. Moreover individual samples from a food series are hereby checked for their quality at defined points in time. Should the result—against all expectations—be negative, the food producer can, by way of a public call, immediately withdraw the entire series from circulation. Since, however, the quality of the respective sample measurement is satisfactory as a rule, it is sufficient for the food producer to record the results in writing and store them. After the investigation however, the tested food samples are usually no longer edible, because the packaging has been opened allowing air to reach the foods. In addition, the storage temperature is usually changed by the investigation, which is not desirable and can have a negative effect on the food. For this reason the food producer must keep a correspondingly large number of samples in order to be able to perform destructive sample measurements at the respective points in time. For this reason the food producer is required to keep a correspondingly large number of samples from a series of food stuffs in store for later investigation. If, for example, the food producer wants to furnish proof of quality for the complete period of the best-before date of a series of food products, he has to investigate, say, m samples at x different time periods, respectively, and therefore he will require, in total, x*m samples (product of x and m=$n_{ges}$ samples), which he has to retain from the series and store. Normally at least two or three samples (m=2 or 3) are tested at any one time in order to achieve statistical reliability. This means that in food production a very large number of samples have to be stored with resulting losses in food production being very big.

With food stuffs in the form of drinks it was found that the existing pressure in the bottle and the bottle material such as glass, china or PET, is crucial to the quality and taste of the drinks.

It is therefore the object of the invention to overcome the above-described disadvantages from the state of the art. In particular it is the object of the invention to propose a method for investigating the shelf life of food stuffs in packagings, which can be carried out at low cost and where the total number ($n_{ges}$=x*m) of food stuffs of a series to be kept in store is kept to a minimum. Further it is an additional requirement of the invention to also propose a device for investigating the shelf life of food stuffs in packagings, with the help of which the disadvantages from the state of the art are at least partially overcome.

The present requirement is met by a method according to the invention for investigating the shelf life of food stuffs in packagings comprising the features of claim 1, in particular from the characterising part. Further, in order to meet the requirement, a device comprising the features of claim 15 is proposed. Preferred further developments of the invention are cited in the dependent method claims and device claims. Features disclosed for the method according to the invention also apply to the device according to the invention and vice-versa. Besides, the method according to the invention can be carried out on the device according to the invention.

The present text mentions the terms "food stuffs" and "packaging", which means that it's all one and the same food stuffs and that these originate from one production series produced at a certain point in time. Besides, these food stuffs are all arranged in the same packagings. The term "sample" refers to the food to be investigated in the packaging. The letters "RM" in the text below mean reference measurement. The letter "M" in the text below means normal (usage) measurement. The two indices "d" and "i" mean direct measurement and indirect measurement.

The method according to the invention for investigating the shelf life of food stuffs comprises at least the following steps:

a) Creating at least one reference measurement comprising:
  a1) a direct and indirect sample measurement RMd,i at the time Tx,
  a2) repetition of the direct and indirect sample measurement RMd,i at predefined time intervals Δt,
  a3) storage of the reference measurement results RMd,i of the sample measurements,
b) Creating a comparison measurement comprising:
  b1) at least one indirect sample measurement Mi at the time Tx,
  b2) comparison of the indirect measurement result Mi with the corresponding reference measurement result RMi from the comparison time Tx,
  b3) performance of at least one direct sample measurement Md at the time Tx, if a deviation of the comparison result from step b2) is exceeded,
  b4) repetition of the indirect sample measurement at predefined time intervals Δt,
  b5) storage of the measurement results Md,i of the sample measurements.

It should be noted that at least initially, step a) for a reference measurement must be completed ahead of step b) for a comparison measurement. It is recommended that for each food product (meaning the same food, e.g. alcohol-free beer of a certain brand) a separate reference measurement is performed according to step a), in order to obtain accurate reference measurements for the later comparison measurement. Ideally, not one, but two or three reference measurements according to step a) are carried out, by means of which it can be ascertained, to what extent the individual reference measurements deviate from each other. Should it be found that there is no deviation, the number of reference measurements for the same food stuff can be minimised, so that ideally only one reference measurement according to step a) needs to be carried out. Furthermore other conditions are specified when taking reference measurements, such as the predefined time intervals $\Delta t$ of individual sample measurements. (In this respect the best-before date may be divided by the desired max. number of sample measurements at the time Tx, from which the predefined time interval $\Delta t$ results.) For example, for a best-before date of 12 months it may be desirable to take only 12 sample measurements at different times. In this case the predefined time interval $\Delta t$ is exactly one month. With the reference measurement in measuring step a1) it is recommended to initially perform an indirect sample measurement RMi at the time Tx, and then the direct sample measurement RMd at the same time Tx. It doesn't matter if the time Tx varies by a few minutes, because normally the minimum best-before date is at least weeks, months or even years in the future. But it is important that the condition for indirect or direct measurement, such as the temperature of the sample (of the food stuff) is the same and that the food stuff is from a series with the same date of manufacture. Also in step a1) an indirect and a direct sample measurement RMd,i on a sample may be taken a number of times at the time Tx in order to be able to exclude measuring errors and measuring tolerances. In step a2) direct and indirect sample measurements RMd,i are then again taken at the time Tx+1 or after the predefined time interval $\Delta t$. Again, only food stuffs from the same series (according to step a1)) are used for the new sample measurement. Measuring itself can be performed as in step a1), but at a later time Tx+1. It also goes without saying that with direct sample measurement normally only food stuffs from a permanently sealed packaging may be used for measuring as a rule. This means that food stuff packagings are excluded, which have previously been destroyed when a measurement was taken in measuring step a1) as part of direct sample measurement/the packagings of which have been opened. In step a2) too, each sample may be subjected to a direct or indirect sample measurement RMd,i a number of times. In step a3) the reference measurement results RMd,i from steps a1) and a2) are stored and archived. It is also feasible that a statistical evaluation (e.g. averaging) of the reference measurement results is carried out as early as when e.g. several sample measurements are directly or indirectly taken from one and the same sample at the same time Tx. In addition attempts may be made to statistically record to what extent the sample measurements RMd,i change from time Tx to time Tx+1 or to further points in time Txy.

In step b) the comparison measurement as such is then performed on the same food products (such as alcohol-free beer of brewery X of brand Y or caffeine-containing lemonade with sugar of brand Z). Here steps a) and b) may overlap at least partially, i.e. it is not necessary to perform a complete reference measurement as per step a) over the entire best-before date, before a first comparison measurement as per step b) begins. Rather it is sufficient for the first reference measurement results RMd,i at the time Tx from step a1) to be present, when step b) of the comparison measurement is started. In step b1) at least one indirect sample measurement Mi as per step a) is performed at the time Tx on the same food stuff from the reference measurement as per step a). Again, indirect sample measurement can be repeated several times in order to exclude measuring errors. Here step b1) is to be performed under the same measuring conditions as measurement Mi at step a1), which means the same investigating conditions, e.g. measured temperature, environmental pressure, air humidity etc. In step b2) the indirect measurement results Mi are compared with the corresponding reference measurement results RMi at the comparison time Tx. Should a distinct deviation be present, e.g. should there be a difference between the measurement results of the reference measurements and the comparison measurements from the same time Tx, then a direct sample measurement Md is also necessary, ideally on the same packaging of the food stuff, on which the indirect sample measurement was performed. Insofar, however, as there are no deviations which have been exceeded between the reference measurement results RMd,i and the direct sample measurement Md,i at the time Tx, a direct sample measurement at the time Tx may be omitted. In order to obtain a higher measuring accuracy, at least one direct sample measurement Md may always be carried out, also during the comparison measurement as per step b) at the time Tx, even if there are no deviations between the reference results and the comparison results. In step b4) a repetition of the direct sample measurements is performed at predefined time intervals $\Delta t$. Conveniently therefore step b4) is not performed until no more measured deviations as per step b3) could be ascertained. Alternatively step b4) may be carried on one and the same sample/food stuff at the time Tx, in order to obtain a higher statistical accuracy. This thus reveals the advantages of the method according to the invention, since the samples during indirect measuring remain undamaged and are available for further measurements. Thus the required number of samples n can be distinctly reduced during ongoing monitoring. Manufacturing losses and storage costs as well as the cost for disposal of the necessary samples can thereby be distinctly reduced. In step b5) the obtained measurement results Md,i from steps b1) to b4) can be stored and retained for further reference.

The present method can be carried out for various food stuffs in various packagings, wherein, however, the method according to the invention should be carried out for each food stuff in its respective packaging, in order to obtain at least exact reference measurements as per step a).

According to the invention provision may be made in that a direct sample measurement of the food stuff is carried out by destroying the packaging. It is feasible for the packaging to be pierced e.g. by a piercing means in order to be able to introduce at least one measuring sensor into the packaging. Due to this measuring sensor it is then possible to measure at least one physical, chemical and/or biological property of the food stuff. This may, for example, be the temperature, the pressure, the moisture, the electrical resistance or other properties of the food stuff, which can be measured directly. Direct sample measurement thus has the advantage that the measured results are not impacted upon by the measuring environment thus excluding any measuring errors. Thus sample measurements can be taken which are highly accurate as regards the measured property of the food stuff. However, direct sample measurement has the disadvantage that, as a rule, the packaging cannot be sealed again, so that at the end of sample measurement, which however can be carried out multiple times at the same time Tx, the food stuff with the packaging is normally unusable, in particular for later measurements. The reason for this is, on the one hand, that after measurements are taken, air gets into the inside of the packaging and, on the other, that e.g. following direct sample measurement overpressure or an inert gas can escape. Moreover, the cooling chain of the measured food sample is normally interrupted by the measurements, as a rule.

Furthermore it is feasible in terms of the invention for indirect sample measurements to be taken on the food stuff, where a non-destructive investigation is performed. The packaging remains intact, as a rule, because the sample measurements are taken exclusively through the sealed packaging. This may include, in particular, the measuring of physical, chemical and/or biological properties of the food stuff through the packaging, preferably without contacting (the food stuff). This can be effected, for example, by way of optical, inductive, capacitive and/or electromagnetic measurements etc. taken with the aid of X-ray or ultrasound techniques or magnetic resonance measurements etc.

Further, provision may be made with the method according to the invention for at least the temperature or the pressure inside the packaging to be measured during a sample measurement. Based on the previously mentioned and measured properties of the food stuff and, as required, the further physical, chemical and/or biological properties of the food stuff, conclusions can then be drawn as to the quality and the taste of the food stuff and thus as to the best-before date.

Based on the reference measurements according to step a) it is known in principle, how the physical, chemical and/or biological properties of the food stuff are changing over time and a limit is reached, where the quality and the taste of the food stuff is no longer sufficient for satisfying the expectations of the food producers. Since at least one of the above mentioned properties of the food stuff substantially changes over time until the end of the best-before date is reached, quality and taste of the food stuff over time can thus also be accurately measured over time.

Furthermore it is feasible in terms of the invention that a $CO_2$ content in the packaging is ascertained from the two measurements of temperature and pressure. This can be done in particular with the aid of a calculating function, where the required input values are at least temperature and pressure in the packaging and where based on these input values the $CO_2$ content in the respective food stuff is then determined. Normally the calculating function for each food stuff (e.g. beer, lemonade etc.) is determined in dependence of temperature or pressure, on the basis of which the corresponding $CO_2$ content in the packaging is then determined. In particular with drinks kept in liquid containers or bottles the $CO_2$ content plays a very important role.

In terms of the invention provision is optionally made for the $CO_2$ content at least in the packaging or in the food stuff to substantially influence the durability. As a result, due to the $CO_2$ content, the best-before date is also substantially influenced. Should the $CO_2$ content in the packaging thus be reduced in the course of time because e.g. a part thereof diffuses through the packaging, the durability of the food stuff also reduces over time. Therefore it is preferably necessary to check the $CO_2$ content in the packaging and/or in the food stuff at regular intervals, for example at predefined time intervals $\Delta t$.

The previously mentioned food stuffs are in particular drinks, i.e. liquid drinks. It is feasible that the drink contains $CO_2$ in particular, which, as already mentioned, has a substantial influence on the quality and the taste of the drink. Thus from the $CO_2$ content unequivocal conclusions can be drawn as to the quality and the taste of the drink and its best-before date to be achieved.

With the method according to the invention provision may be optionally made that in a step o1) prior to a sample measurement, the packaging with the food stuff is at least shaken or is brought up to a predefined temperature in order to achieve a state of equilibrium inside the packaging. The state of equilibrium inside the packaging is of major importance for an accurate sample measurement both for indirect and for direct measuring. Otherwise there is the chance that serious measuring errors might occur during sample measurement (RMd,i or Md,i), so that the sample measurement is altogether unusable. In particular with carbonated drinks a uniform partial pressure in the gas space and the liquid space of the packaging is obtained by shaking.

Preferably with the method according to the invention, the previously mentioned step o1) of shaking the sample takes place at least simultaneously with or prior to (in terms of time) step a1) or b1). Thus it can be achieved that prior to the respective sample measurement according to step a1) and/or b1) a state of equilibrium in the packaging is reached making it possible for the measurement results to be very accurate. Also the packaging with the food stuff may be brought up to a predefined temperature thereby excluding measuring errors directly due to temperature. It is recommended that a homogeneous temperature exists also within the packaging.

Furthermore, provision may be made according to the invention that in a step o2) prior to at least one sample measurement, at least one geometric property of the packaging is recorded by way of measuring. The said geometric property may be the external dimensions of the packaging, in particular the dimensions in the measuring area, e.g. the bottle neck or the head area. As such the external diameter of a drinks bottle neck can be recorded by way of measuring. Also the wall thickness of the packaging in the measuring area can be technically measured in order to be able to perform exact measuring within the packaging. Here the internal diameter of a bottle neck in the measuring area can e.g. be determined, on the basis of which the run length of the light beam can be determined. But also the refractive index of the packaging material of the packaging can be recorded by means of measuring. Overall, recording the geometric properties of the packaging is useful for permitting indirect sample measurements, or in other words, for excluding measuring errors due to geometric packaging tolerances.

Further, with the method according to the invention, provision may be made for using the same packaging for first performing an indirect, and then a direct sample measurement RMd,i or Md,i at the time Tx. With this arrangement it is feasible that the indirect sample measurement RMi or Mi is repeated a number of times in succession in order to be able to form e.g. a statistical mean value. Once the indirect sample measurement RMi or Mi has taken place, the same package can be used for performing the direct sample measurement RMd or Md, which as a rule means the destruction of the packaging. This direct sample measurement can also be repeated a number of times in order to obtain again a statistical mean value. This course of action can be pursued both in step a1) and in steps b1) and b3). It is also feasible that indirect and direct measuring on the sample is carried out simultaneously, wherein it must be ensured that direct sample measuring does not lead to a change in the physical, chemical and/or biological properties of the food stuff in the packaging. Therefore it must be avoided that direct sample measuring is finished before indirect sample measuring has been completed.

With the invention it is further possible for the indirect sample measurement of the food stuff to take place by means of at least one optical measurement through the packaging. This optical measurement does not necessarily have to be performed within the light range visible to humans. The infrared or ultra-violet range of radiation is also perfectly acceptable for taking measurements. Other electromagnetic spectra of light are also feasible. Or, as mentioned above, it is possible to use ultrasound or X-rays for taking measurements.

Furthermore it is feasible in terms of the method according to the invention that the packaging is, at least partially, transparent to light or that it comprises at least an optically transparent window for measuring. This optically transparent area does not have to be transparent to the human eye, it suffices if the above-described optical measurements can penetrate it in order to be able to record, by way of measuring, the properties of the food stuffs in the packaging, without incurring measuring errors if possible. It goes without saying that a respective optical sensor takes measurements geometrically in the optically transparent area of the packaging. To this end a respective light source emitting the optical rays may be arranged on an opposite side of the optical sensor. Also a number of optical sensors and light sources for performing the method according to the invention are, of course, feasible, wherein not all of these need necessarily function in the same frequency spectrum or on the same wavelength. On the contrary, taking optical measurements may be made easier by light sources which at least at times, emit different types of light of different wavelength. Also optical measurements can be taken using monochromatic, polarised and/or pulsed light etc.

In addition, with the method according to the invention it may be feasible for the packaging to receive and enclose the food stuff in a pressure-tight manner. The packaging may be configured in particular as a bottle or liquid container. Normally such a packaging comprises a lid through which the liquid, in particular in the form of a drink, can be poured from the packaging.

Furthermore the present invention is directed at a device for investigating the shelf life of food stuffs in packagings. The previously mentioned method according to the invention may be carried on this device.

In terms of the device according to the invention it is further feasible that the mechanical mounting for the packaging is provided simultaneously with a rotating and/or swiveling mechanism. Using this rotating or swiveling mechanism the packaging can be shaken in order to achieve a state of equilibrium within the packaging allowing it perform accurate sample measurements.

Further, with the device according to the invention, provision may be made for the mechanical mounting of the packaging to be provided simultaneously with the rotating and/or swiveling mechanism. Thus due to the mechanical mounting the packaging can be fixed securely to the rotating and/or swiveling mechanism. The rotating and/or swiveling mechanism therefore also rotates the mechanical mounting, which again makes the packaging with the food stuff move. For this purpose a respective drive motor may be provided on the device, which drives the rotating and/or swiveling mechanism in an electromagnetic manner.

Furthermore, provision may be made with the device according to the invention for the measuring head to be provided with a piercing means thereby making it possible to perform direct measurements with at least one sensor in the packaging. Ideally this measuring head is also arranged on the rotating and/or swiveling mechanism and is thus also rotated by this together with the packaging. Using the previously mentioned piercing means it is possible to arrange a sensor inside the packaging and thus to perform direct measurements. Ideally however, the piercing means/the respective measuring head continue to keep the packaging sealed, thereby preventing e.g. an overpressure in the packaging from escaping. Also in case the food stuff is a liquid, this cannot escape from the packaging via the sealed piercing means. All the same, it is possible to insert a measuring sensor as far as into the food stuff itself, and thus to directly measure the physical, chemical and/or biological properties inside the food stuff. It goes without saying that a number properties of the food stuff can be recorded by measuring, wherein one or more sensors may be employed for measuring further properties. As such the temperature and the pressure inside the food stuff may be measured. The electrical resistance of the food stuff for example as well as further properties of it may be recorded in a simple manner.

With the device according to the invention it is also feasible for at least one of the following sensors to be present: temperature sensor, pressure sensor, optical sensor, weight sensor, humidity sensor, capacitive or inductive sensor, resistance sensor etc. This sensor may be integrated with the device and/or the measuring head. Further, it is feasible that the sensor be inserted into the packaging via the piercing means. Also as number of sensors may be arranged in the device or in the measuring head of the device. Also so-called combi-sensors able to measure a number of properties may be used.

In terms of the device according to the invention it is also possible that at least one light source, in particular in the form of a laser, is present and that the emitted light from a light source can be recorded by an optical sensor by way of measuring. Also a number of light sources may of course be arranged geometrically to each other in the device in order to be able to optically record, by way of measuring, a measuring section or field. Here so-called line sensors or array sensors, acting as optical sensors, can record light emitted from the light source by way of measuring. Control of the light source as well as an evaluation of the signals recorded by way of measuring from the one or more optical sensors can be effected by the evaluation unit in the device. At the same time the obtained optical data can be compared with measured data from a sensor arranged inside the packaging, and processed and/or stored. It goes without saying however, that optical measurements can also be carried out separately from the direct sample measurements.

Furthermore it is feasible, according to the invention, for the device to comprise at least one tempering unit for tempering the packaging with the food stuff. The tempering unit is used, to bring the packaging with the food stuff up to a predefined temperature, thereby avoiding measuring errors caused by differences in temperature. Thus it is possible, at least with indirect non-destructive sample measuring, that cooling of the food stuff during measuring is not interrupted.

BRIEF DESCRIPTION OF THE SEVERAL VIEWS OF THE DRAWINGS

Further measures and advantages of the invention are revealed in the claims, the description below and the drawings. Further, the features disclosed for the device according to the invention also apply to the method according to the invention and vice-versa. In the drawings the invention is depicted by way of a schematic exemplary embodiment.

Features from the claims and the description may be essential to the invention both on their own and in any given combination.

In the drawing:

FIG. 1 shows a schematic view of a device according to the invention for investigating the shelf life of food stuffs in packagings, and FIG. 2 shows an exemplary diagram for sample consumption according to the state of the art (NS) and according to the method according to the invention (NE).

DESCRIPTION OF SPECIFIC EMBODIMENTS OF THE INVENTION

Figure 1:
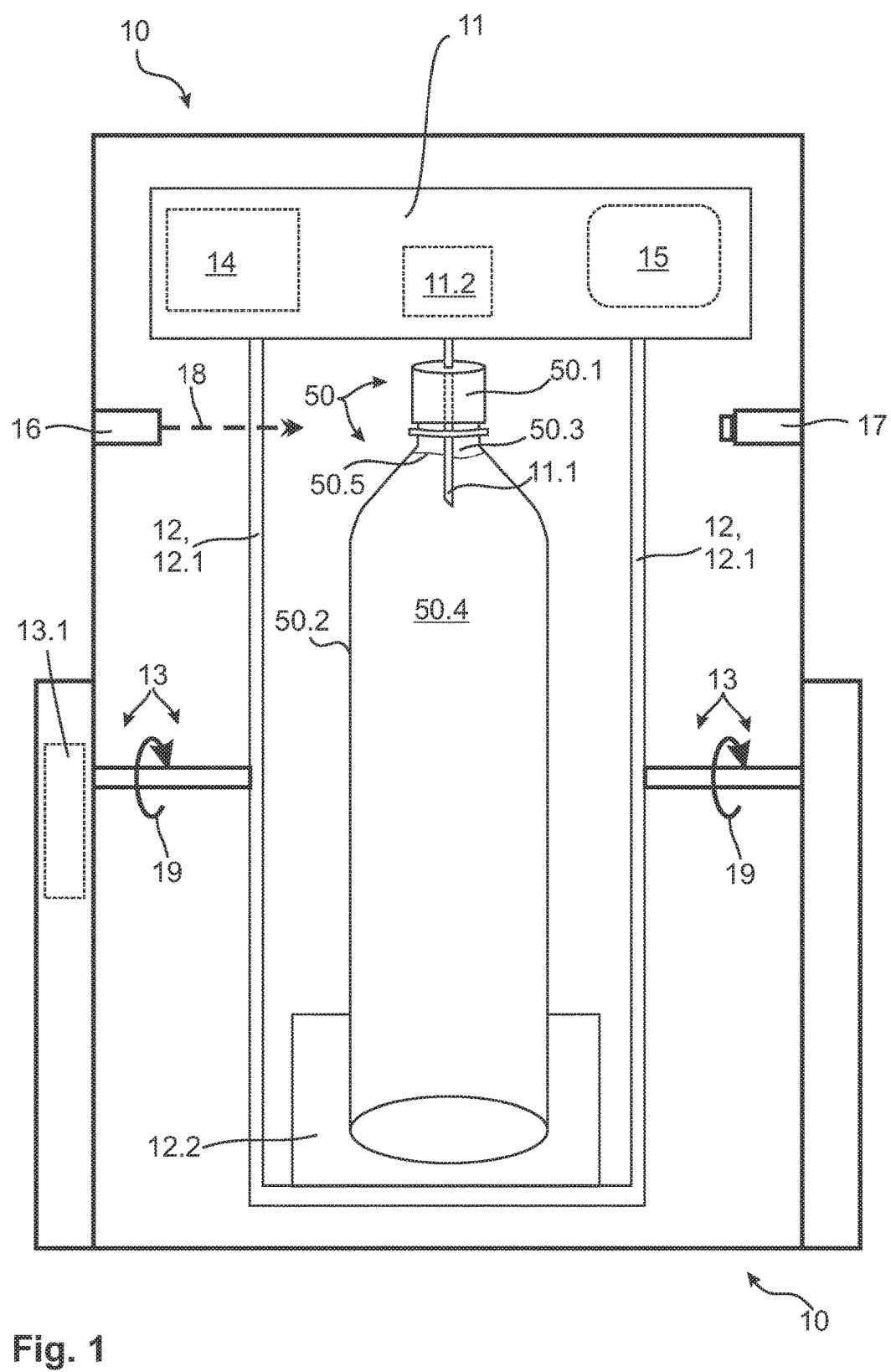

FIG. 1 schematically shows a side view of a device 10 according to the invention for investigating the shelf life of food in packagings. This device 10 comprises a mechanical mounting 12 for the packaging 50 to be measured and which contains the respective food stuff 50.4. The packaging 50 to be measured is in particular a liquid container in form of a bottle 50.2, which is closed by a lid 50.1. The food stuff 50.4 in form of a drink has been filled into the bottle 50.2. A filling level 50.5 of the drink in the bottle 50.2 is also schematically indicated. Above the filling level 50.5 there is a head space 50.3, which is normally filled, not with the food stuff 50.4, but with a gaseous medium which normally contains $CO_2$. In order to prevent this gas in the head space 50.3 from escaping, the bottle 50.2 is sealed with the lid 50.1.

As can further be seen in FIG. 1, the packaging 50 has been pierced by a piercing means 11.1, which protrudes through the lid 50.1 for example into the drink 50.4. In terms of the invention it is however sufficient if the piercing means 11.1 passes through the lid 50.1 only as far as the head space 50.3 of the bottle 50.2. The piercing means 11.1 itself belongs to the measuring head 11, which is located above the lid 50.1. The measuring head 11 may also be used for sealing the lid 50.1 during piercing by the piercing means 11.1, which in the present case, however, is not revealed in FIG. 1 for better understanding of the invention. The measuring head 11 which belongs to the device 10 according to the invention may have at least one sensor 11.2 arranged in it. This sensor 11.2 may, in particular, be a temperature sensor and/or a pressure sensor. Also a number of sensors 11.2 may be arranged in the measuring head 11, which directly record the properties of the food stuff 50.4 via the piercing means 11.1 by way of measuring. Furthermore the device 10 is equipped with a rotating and/or swiveling mechanism 13, which is shaped in a more or less frame-like 12.1 manner and which receives/fixes the packaging 50 securely via the mechanical mounting 12. At the lower end of the frame 12.1 of the mechanical mounting 12 a holder 12.2 is arranged, which is used for holding the packaging 50 in a form-locked and/or force-locked manner. Due to this mechanical mounting 12 the packaging 50 can be adjusted within the measuring device 10 so that it is geometrically accurate. The measuring head 11, which on the rotating and/or swiveling mechanism 13 is also connected with the frame 12.1 of the mechanical mounting 12, may additionally comprise an evaluation unit 14 and a display 15. It is also feasible for at least one evaluation unit 14 or a corresponding display 15 to be fixedly arranged within the device 10, i.e. independently of the rotating and/or swiveling mechanism.

Instead of the frame 12.1 a closed housing may be used as a mechanical mounting 12, which may contain also the above-described tempering unit for the packaging 50. This tempering unit is however not shown in FIG. 1.

Furthermore, at least one light source 16, e.g. in form of a laser, may be arranged inside the device 10, in particular in the area of the head space 50.3 of the bottle 50.2, which emits a light beam 18 radiating through the packaging 50. On the side of the packaging 50 opposite the light source 16 an optical sensor 17 may be arranged inside the device 10, which detects the emitted light beam 18 by way of measuring. Or an optical sensor 17 may be provided on the light source 16 itself, which measures part of the reflected light beam 18 of the light source 16. Due to the proposed light source 16 as well as the optical sensor 17, non-destructive indirect sample measuring RMi and Mi of the packaging 50 with the food stuff 50.4 may be performed. As already mentioned the emitted light beam 18 is not limited to light visible to the human eye. Light beams 18 of a different wavelength are also feasible.

In order to achieve optimal sample preparation, the device 10 is provided with the already mentioned rotating and/or swiveling mechanism 13. This is driven by an electronic drive 13.1 which for example may be realised by an E-motor. The rotating and/or swiveling mechanism 13 rotates the mechanical mounting 12 with the fixed packaging 50 and the measuring head 11 arranged on the mechanical mounting 12. It is also feasible that at least one light source 16 and/or one optical sensor 17 is arranged on the mechanical mounting 12, which is not fixedly connected to the device 10, as shown in FIG. 1.

Figure 2:
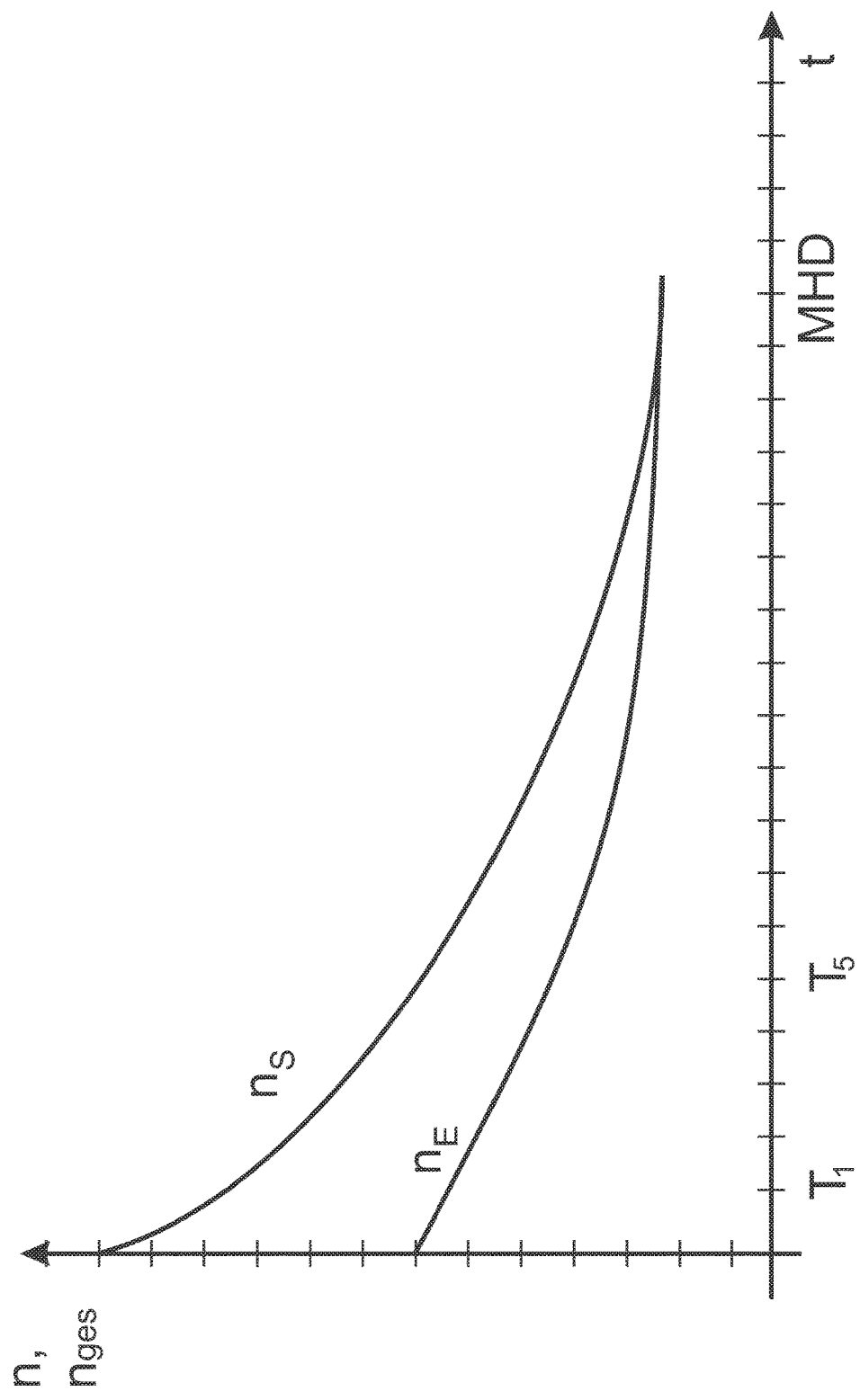

FIG. 2 shows purely schematically a diagram of a comparison of the reduced number of samples $n_E$ of the method according to the invention with the number of samples $n_S$ from the state of the art. It clearly shows that the number of samples $n_E$ can be halved, quartered or even further reduced by the method according to the invention, which results in the already described advantages of the invention.

LIST OF REFERENCE SYMBOLS 10 device
11 measuring head
11.1 piercing means
11.2 sensor, in particular temperature/pressure and humidity sensor
12 mechanical mounting for 50
12.1 frame with mounting for 50
12.2 holder for 50
13 rotating and/or swiveling mechanism
13.1 drive
14 evaluation unit
15 display
16 light source, in particular laser
17 optical sensor for 16
18 arrow for light beam
19 arrow for direction of rotation
50 packaging
50.1 lid
50.2 bottle, liquid container
50.3 head space
50.4 food stuff, in particular drink
50.5 filling level

What is claimed is:

1. A method for investigating the shelf life of food stuffs (50.4) in packagings (50),
wherein the following steps are performed:
a) creating at least one reference measurement comprising:
a1) a direct and indirect sample measurement RMd,i at the time Tx, a2) repetition of the direct and indirect sample measurement RMd,i at predefined time intervals Δt,
a3) storage of the reference measurement results RMd,i of the sample measurements,
b) creating a comparison measurement comprising:
b1) at least one indirect sample measurement Mi at the time Tx,
b2) comparison of the indirect measurement result Mi with the corresponding reference measurement result RMi from the comparison time Tx,
b3) performance of at least one direct sample measurement Md at the time Tx, if a deviation of the comparison result from step b2) is exceeded,
b4) repetition of the indirect sample measurement at predefined time intervals Δt,
b5) storage of the measurement results Md,i of the sample measurements.

2. The method according to claim 1, wherein a direct sample measurement of the food stuff (50.4) is performed by destroying the packaging (50), wherein in particular the packaging (50) is pierced in order to insert at least one measuring sensor (11.2) into the packaging (50), in order to measure at least one physical, chemical and/or biological property of the food stuff (50.4).

3. The method according to claim 1, wherein an indirect sample measurement of the food stuff (50.4) is performed, wherein a non-destructive investigation takes place and the packaging (50) remains undamaged,
wherein in particular physical, chemical and/or biological properties of the food stuff (50.4) are measured preferably contactless through the packaging (50).

4. The method according to claim 1, wherein at least the temperature or the pressure is measured during the sample measurement.

5. The method according to claim 1, wherein a $CO_2$ content in the packaging (50) is ascertained from the measured values RMd,i/Md,i of the temperature and the pressure in particular via a calculating function.

6. The method according to claim 1, wherein in a step o1) prior to a sample measurement, the packaging (50) with the food stuff (50.4) is at least shaken or brought up to a predefined temperature in order to achieve a state of equilibrium.

7. The method according to claim 1, in a step o1), the packaging (50) with the food stuff (50.4) is at least shaken or brought up to a predefined temperature in order to achieve a state of equilibrium, and is performed simultaneously with at least step a1) or b1).

8. The method according to claim 1, wherein in a step o2) prior to at least one sample measurement, at least one geometric property of the packaging (50) is recorded by way of measuring.

9. The method according to claim 1, wherein initially an indirect and then a direct sample measurement RMd,i/Md,i is performed on the same packaging (50) at the time Tx.

10. The method according to claim 1, wherein an indirect sample measurement of the food stuff (50.4) is performed by means of at least one optical measurement through the packaging (50).

11. The method according to claim 1, wherein the food stuff (50.4) is a drink, in particular a carbonated drink.

12. The method according to claim 1, wherein the packaging (50) is configured to be at least partially transparent or comprises at least one optically transparent measuring window.

13. The method according to claim 1, wherein the packaging (50) holds and encloses the food stuff (50.4) in a pressure-tight manner, wherein in particular the packaging (50) is configured as a bottle (50.2) or a liquid container.

* * * * *